US00PP28096P3

(12) United States Plant Patent
Wood

(10) Patent No.: US PP28,096 P3
(45) Date of Patent: Jun. 13, 2017

(54) ***SPIRAEA* PLANT NAMED 'SMNSNFD'**

(50) Latin Name: *Spiraea nipponica*
Varietal Denomination: SMNSNFD

(71) Applicant: Timothy Wood, Spring Lake, MI (US)

(72) Inventor: Timothy Wood, Spring Lake, MI (US)

(73) Assignee: Spring Meadow Nursery, Inc, Grand Haven, MI (US)

( * ) Notice: Subject to any disclaimer, the term of this patent is extended or adjusted under 35 U.S.C. 154(b) by 40 days.

(21) Appl. No.: 14/756,866

(22) Filed: Oct. 22, 2015

(65) Prior Publication Data

US 2017/0118890 P1 Apr. 27, 2017

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Keith Robinson
(74) *Attorney, Agent, or Firm* — Cassandra Bright

(57) ABSTRACT

A new and distinct *Spiraea* cultivar named 'SMNSNFD' is disclosed, characterized by a uniquely compact plant habit, easy, vigorous growth, without developing a rangy habit. Plants have a strong flowering habit. The new variety is a *Spiraea*, normally produced as an outdoor garden or container plant.

3 Drawing Sheets

Latin name of the genus and species: *Spiraea nipponica*. Variety denomination: 'SMNSNFD'.

BACKGROUND OF THE INVENTION

The new *Spiraea* cultivar is a product of a planned breeding program conducted by the inventor, Timothy D. Wood, in Grand Haven, Mich. The objective of the breeding program was to produce new *Spiraea* varieties of compact and full habit with new and better flower and leaf colors. The open pollination resulting in this new variety was made during 2007.

The seed parent is the unpatented commercial variety *Spiraea nipponica* 'Flachenfuller' The pollen parent is unknown, as it was an open pollination breeding program. The new variety was identified as a potentially interesting selection in 2009, at a greenhouse in Grand Haven, Mich.

Asexual reproduction of the new cultivar 'SMNSNFD' by softwood cuttings was first performed during the Summer of 2013, at a commercial greenhouse in Grand Haven, Mich. Subsequent propagation has shown that the unique features of this cultivar are stable and reproduced true to type in successive generations.

SUMMARY OF THE INVENTION

The cultivar 'SMNSNFD' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNSNFD' These characteristics in combination distinguish 'SMNSNFD' as a new and distinct *Spiraea* cultivar:

1. Very strong flowering.
2. Uniquely compact habit.

3. Vigorous and easy to grow, without excessive rangy growth.

PARENT COMPARISON

Plants of the new cultivar 'SMNSNFD' are similar to plants of the seed parent, *Spiraea nipponica* 'Flachenfuller' in most horticultural characteristics, however, plants of the new cultivar 'SMNSNFD' differ in the following;

1. More compact
2. Stronger flowering.
3. Stronger plant.

Pollen parent unknown as this is a product of open pollination.

COMMERCIAL COMPARISON

Plants of the new cultivar 'SMNSNFD' can be compared to the unpatented commercial variety *Spiraea* 'Snowmound'. These varieties are similar in most horticultural characteristics; however 'SMNSNFD' differs in the following:

1. More compact plant form
2. Stronger flowering.
3. Stronger plant.

BRIEF DESCRIPTION OF THE PHOTOGRAPHS

The accompanying photograph in FIG. 1 illustrates in full color a typical plant of 'SMNSNFD' grown in an outdoor bed, in Grand Haven, Mich.

Figure 1:
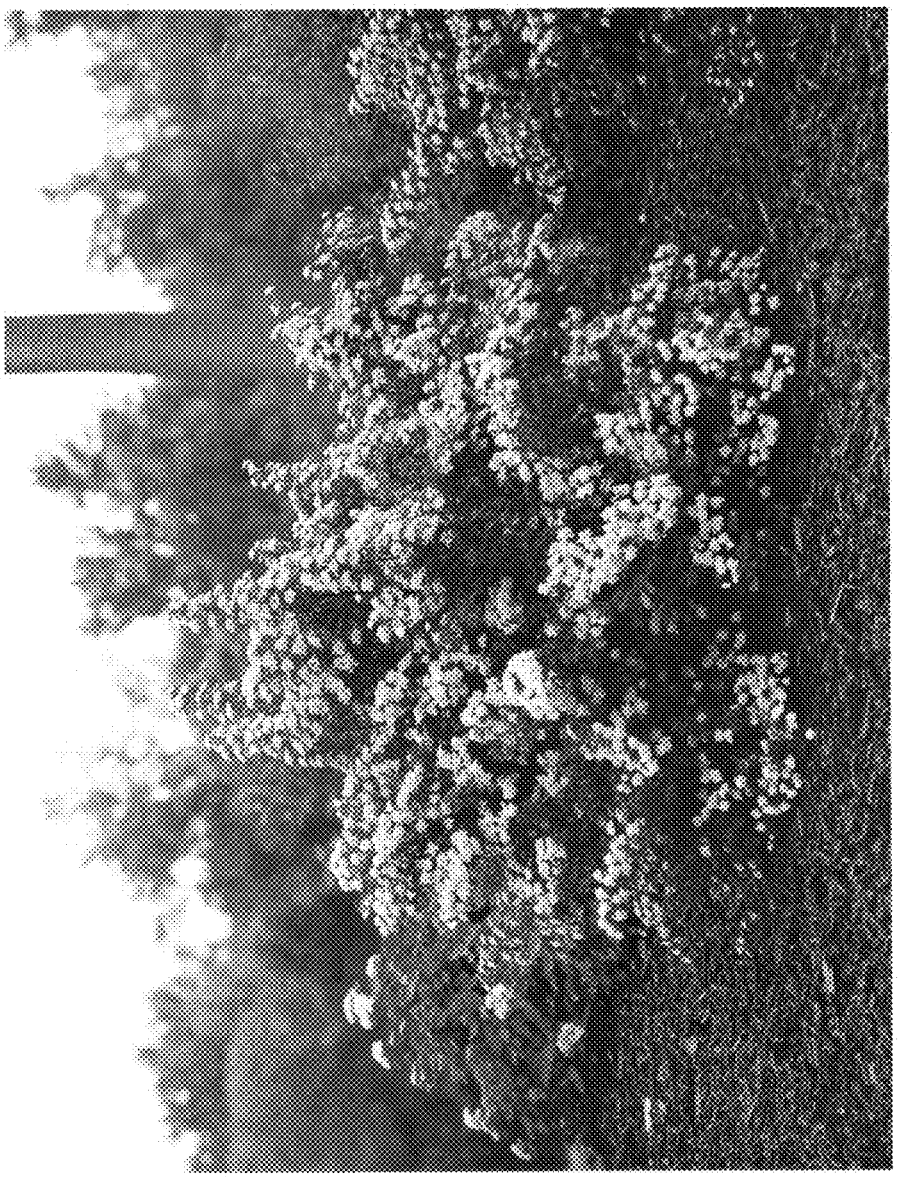
Figure 2:
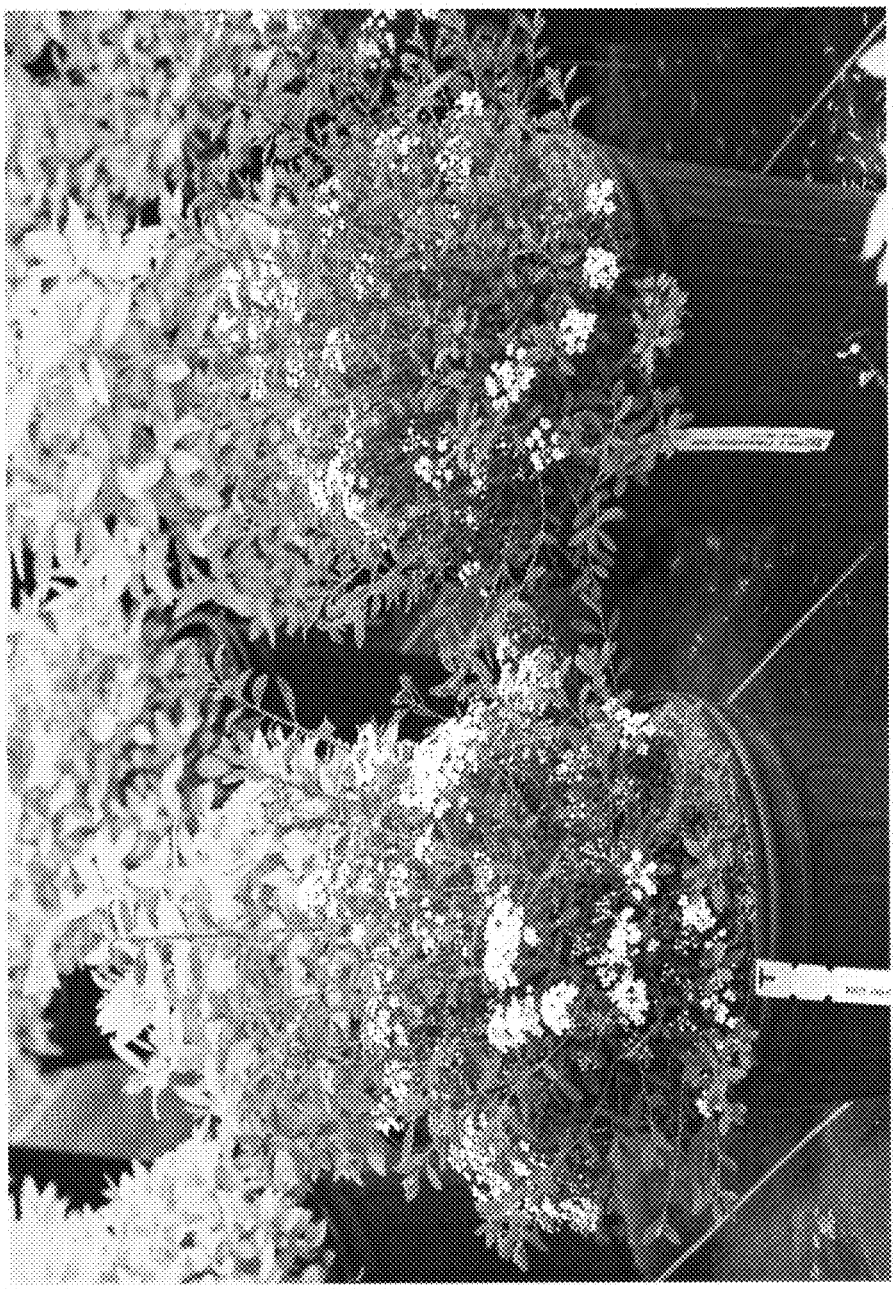
FIG. 2 illustrates plants grown in containers.
Figure 3:
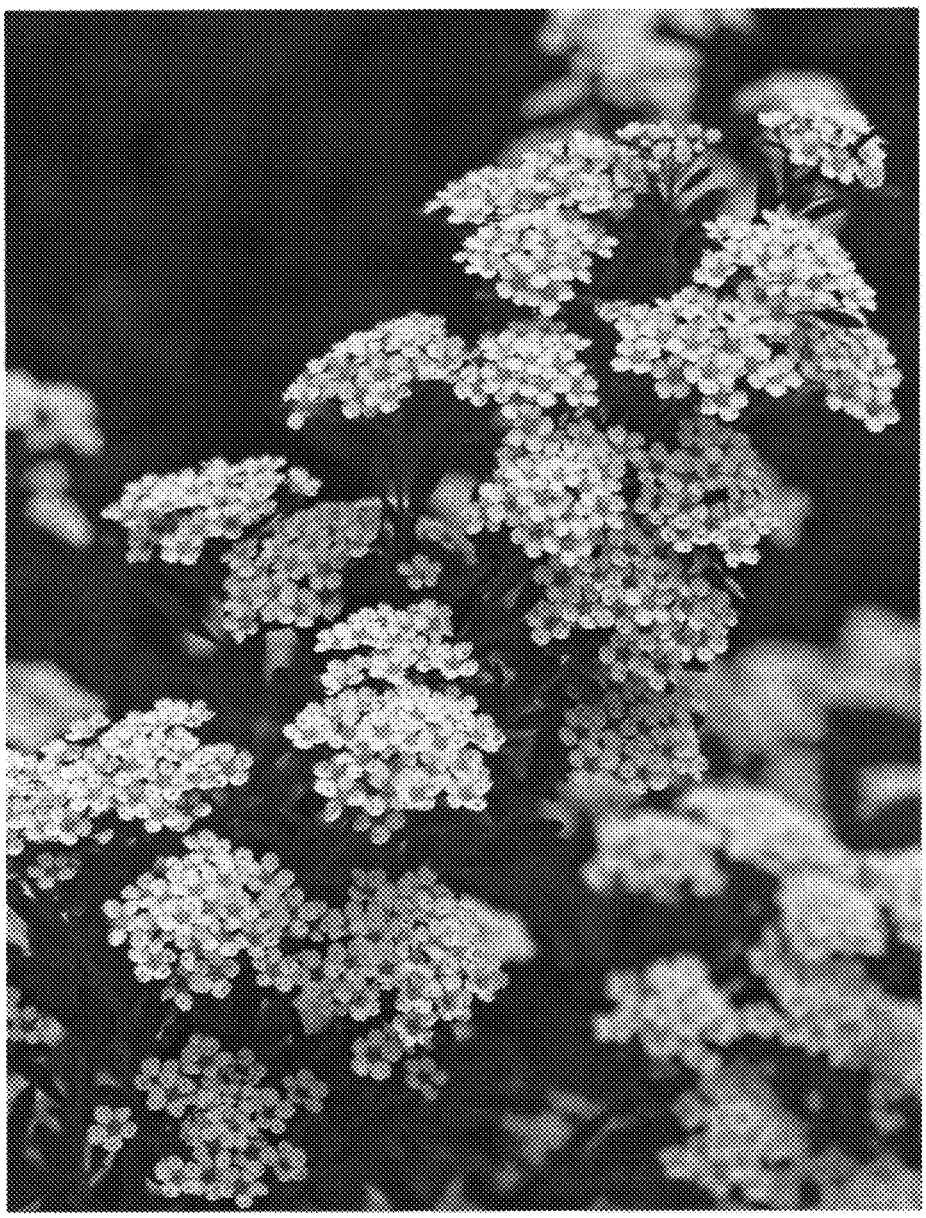
FIG. 3 illustrates in full color a typical inflorescence of 'SMNSNFD'. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'SMNSNFD' plants grown in a commercial double poly greenhouse in Grand Haven, Mich. under natural lighting. Measurements were taken during Spring of 2015. The plants were 2 years old in 2 gallon containers. The growing temperature ranged from 5° C. to 27° C. Measurements and numerical values represent averages of typical plant types.

Botanical classification: *Spiraea nipponica* 'SMNSNFD'.

PROPAGATION

Time to initiate roots: About 25 days at approximately 24° C.

Root description: Fibrous and fleshy, moderate to dense density medium thickness and freely branching. White to brown in color, not effectively measured with a color chart.

Time to produce a rooted young plant: About 2 months at 24° C.

PLANT

Plant type: Perennial shrub.
Age of plant described: Approximately 2 years old.
Growth habit: Rounded.
Pot size of plant described: 2 gallon pot.
Overall plant shape: Upright and rounded.
Height: Approximately 56 cm to top of foliage.
Plant spread: Approximately 40 cm.
Growth rate: Moderate to fast.
Plant vigor: Good.
Branching characteristics: Upright, branching occurs at pinching. Pinching required.
Length of primary lateral branches: Approximately 27 cm mature growth.
Diameter of lateral branches: Approximately 4.0 cm for mature growth.
Quantity of lateral branches: About 5 lateral branches per main branch.
Stem:
- *Stem appearance*.—Square.
- *Stem strength*.—Good.
- *Stem color*.—Top: Near RHS Green 143C. Underside: Near RHS Red-purple 61B.
- *Pubescence*.—None.
- *Aspect*.—0-90°.

Internode length: Average 1.5 cm.

FOLIAGE

Leaf:
- *Arrangement*.—Sub-alternate, single.
- *Leaf shape*.—Oblancolate.
- *Average length*.—Approximately 2.7 cm.
- *Average width*.—Approximately 0.8 cm.
- *Apex*.—Rounded.
- *Base*.—Cuneate.
- *Margin*.—Crenate at tip but ¼ way down the leaf margin turns to entire.
- *Texture of top surface*.—Smooth, waxy.
- *Texture of bottom surface*.—Smooth, waxy.
- *Color*.—Young foliage upper side: Near RHS Yellow-green 144A. Young foliage under side: Near RHS Yellow-green 144A. Mature foliage upper side: Near RHS Green 141A. Mature foliage under side: Near RHS Green 143A.
- *Venation*.—Pattern: Pinnate. Color upper side: Near RHS Green 141A. Color under side: Near RHS Green 143A.
- *Petiole*.—Average Length: Approximately 3 mm. Diameter: <1 mm. Petiole color upper side: Near RHS Yellow-green 145B. Petiole color lower side: Near RHS Yellow-green 145B. Petiole Texture upper side: Smooth, waxy. Petiole Texture lower side: Smooth, waxy.

FLOWER

Natural flowering season: Spring.
Inflorescence type and habit: Single rotate flowers located on terminal corymbs.
Flower arrangement: Single rotate flowers.
Quantity of flowers per inflorescence: Average 12-20.
Inflorescence size:
- *Width*.—Approximately 2 cm.
- *Height*.—Approximately 1.5 cm.

Quantity of flowers per lateral stem: 210.
Quantity of flowers per plant: 1,000.
Individual flowers:
Flower form: Rotate.
Flower aspect: Upright and outward.
Flowering habit: Terminal.
Size:
- *Diameter*.—Approximately 6 mm.
- *Length*.—Approximately 20 mm.
- *Depth*.—Approximately 2 mm.

Flower other characteristics:
- *Persistence*.—Self cleaning.
- *Fragrance*.—None.

Petal:
- *Petal arrangement*.—Single whorl of five petals, not fused.
- *Petal appearance*.—Smooth, opaque.
- *Number of petals per flower*.—5.
- *Petal shape*.—Widely elliptic.
- *Petal base*.—Obtuse.
- *Margin*.—Entire.
- *Tip shape*.—Obtuse.
- *Length*.—3 mm.
- *Width*.—3 mm.
- *Texture*.—Upper: Smooth. Lower: Smooth.

Petal color:
- *When opening*.—Upper surface: Near RHS White 155A. Lower surface: Near RHS White 155A.
- *Fully opened*.—Upper surface: Near RHS White 155A. Lower surface: Near RHS White 155A.

Bud:
- *Shape*.—Round.
- *Length*.—Approximately 2 mm.
- *Diameter*.—Approximately 2 mm.
- *Color*.—Near RHS Yellow-green 150D.

Sepals:

*Shape*.—Triangular.

*Appearance*.—Smooth, opaque.

*Arrangement*.—Single whorl of 5 sepals.

*Number of sepals*.—5.

*Length*.—Approximately 2 mm.

*Width*.—Approximately 2 mm.

*Margin*.—Entire.

*Base*.—Truncate.

*Tip*.—Cunate.

*Texture*.—Smooth.

*Color*.—Upper side: Near RHS Yellow-green 144A. Lower side: Near RHS Yellow-green 144A.

Calyx:

*Shape*.—Single whorl of five.

*Length*.—3 mm.

*Diameter*.—3 mm.

Peduncle:

*Length*.—8 mm.

*Diameter*.—1 mm.

*Color*.—Near RHS Yellow-Green 144C

*Orientation*.—10-90°.

*Strength*.—Good.

*Texture*.—Smooth, waxy.

Pedicel:

*Length*.—7 mm.

*Diameter*.—Less than 1 mm.

*Color*.—Near RHS Yellow-Green 144C.

*Orientation*.—45-90°.

*Strength*.—Good.

*Texture*.—Smooth, waxy.

REPRODUCTIVE ORGANS

Stamens:

*Number*.—Approximately 11.

*Filament length*.—2 mm.

*Filament color*.—Near RHS White 155B.

Anthers:

*Shape*.—Round.

*Length*.—Less than 1 mm.

*Color*.—Near RHS Brown 200A.

Pistil:

*Number*.—6.

*Length*.—Less than 1 mm.

*Style*.—Length: Approximately 1 mm. Color: Near RHS White 155C.

*Stigma*.—Shape: Rounded. Color: Near RHS White 155C. Ovary color: Near RHS Yellow 9A.

OTHER CHARACTERISTICS

Seeds and fruits: Not observed to date.

Garden performance: Excellent performance in a garden setting.

Disease/pest resistance: Neither resistance nor susceptibility to normal diseases and pests of *Spiraea* have been observed.

Temperature tolerance: The new variety tolerates temperatures between −31° C. to 38° C.

What is claimed is:

1. A new and distinct cultivar of *Spiraea* plant named 'SMNSNFD' as herein illustrated and described.

* * * * *